US011464748B2

(12) United States Patent
Lam et al.

(10) Patent No.: US 11,464,748 B2
(45) Date of Patent: Oct. 11, 2022

(54) PARTICLES FOR TARGETED DELIVERY AND USES IN MANAGING BLEEDING OR BLOOD CLOTTING

(71) Applicants: Emory University, Atlanta, GA (US); Georgia Tech Research Corporation, Atlanta, GA (US); Chapman University, Orange, CA (US); Children's Healthcare of Atlanta, Inc., Atlanta, GA (US)

(72) Inventors: Wilbur A. Lam, Decatur, GA (US); Caroline Hansen, Atlanta, GA (US); Yumiko Sakurai, Atlanta, GA (US); Andrew Lyon, Irvine, CA (US)

(73) Assignees: Emory University, Atlanta, GA (US); Children's Healthcare of Atlanta, Inc., Atlanta, GA (US); Georgia Tech Research Corporation, Atlanta, GA (US); Chapman University, Orange, CA (US)

(*) Notice: Subject to any disclaimer, the term of this patent is extended or adjusted under 35 U.S.C. 154(b) by 596 days.

(21) Appl. No.: 16/074,643

(22) PCT Filed: Jan. 31, 2017

(86) PCT No.: PCT/US2017/015872
§ 371 (c)(1),
(2) Date: Aug. 1, 2018

(87) PCT Pub. No.: WO2017/136356
PCT Pub. Date: Aug. 10, 2017

(65) Prior Publication Data
US 2020/0306199 A1 Oct. 1, 2020

Related U.S. Application Data

(60) Provisional application No. 62/289,642, filed on Feb. 1, 2016.

(51) Int. Cl.
*A61K 9/50* (2006.01)
*A61K 38/37* (2006.01)

(52) U.S. Cl.
CPC .......... *A61K 9/5031* (2013.01); *A61K 9/5036* (2013.01); *A61K 9/5073* (2013.01); *A61K 9/5089* (2013.01); *A61K 38/37* (2013.01)

(58) Field of Classification Search
None
See application file for complete search history.

(56) References Cited

U.S. PATENT DOCUMENTS

| | | | |
|---|---|---|---|
| 4,652,441 A * | 3/1987 | Okada | B01J 13/125 424/497 |
| 5,330,974 A | 6/1994 | Pines | |
| 6,231,892 B1 | 5/2001 | Hubbell | |
| 6,391,343 B1 * | 5/2002 | Yen | A61K 9/1611 424/491 |
| 6,552,172 B2 | 4/2003 | Marx | |
| 2005/0129727 A1 | 6/2005 | Weber | |
| 2008/0311177 A1 * | 12/2008 | Hammond | A61K 38/1825 424/443 |
| 2010/0028402 A1 | 2/2010 | Dobrovolskaia | |
| 2014/0093575 A1 | 4/2014 | Hammond | |
| 2015/0004205 A1 | 1/2015 | Elbert | |
| 2015/0064267 A1 | 3/2015 | Ramamurthi | |
| 2015/0290092 A1 | 10/2015 | Shieh | |

FOREIGN PATENT DOCUMENTS

| | | |
|---|---|---|
| CA | 2688047 | 8/2012 |
| RU | 2369386 | 10/2009 |

OTHER PUBLICATIONS

Volodkin et al., Matrix Polyelectrolyte Microcapsules: New System for Macromolecule Encapsulation, Langmuir 2004, 20, 3398-3406 (Year: 2004).*
Shutava et al., Layer-by-Layer-Coated Gelatin Nanoparticles as a Vehicle for Delivery of Natural Polyphenols ACS Nano, vol. 3, No. 7, 1877-1885, 2009 (Year: 2009).*
Brown et al. Ultrasoft microgels displaying emergent, platelet-like, behaviors, Nat Mater. 2014, 13(12): 1108-1114.
De Geest et al. Layer-by-layer coating of degradable microgels for pulsed drug deliveryJournal of Controlled Release 116 (2006) 159-169.
Hanafy et al. Control of colloidal CaCO3 suspension by using biodegradable polymers during fabrication, Beni-Suef University Journal of Basic and Applied Sciences, 2015, vol. 4, Issue 1, pp. 60-70.
Hansen et al. Platelet-Microcapsule Hybrids Leverage Contractile Force for Targeted Delivery of Hemostatic Agents, ACS Nano, 2017, 11, 5579-5589.
Hu et al. Engineering platelet-mimicking drug delivery vehicles, Front. Chem. Sci. Eng. 2017, 11(4): 624-632.
Korin et al. Shear-Activated Nanotherapeutics for Drug Targeting to Obstructed Blood Vessels, Science, 2012, 337 (6095):738-42.
Rejinold et al. Development of novel fibrinogen nanoparticles by two-step co-acervation method, International Journal of Biological Macromolecules 47 (2010) 37-43.

(Continued)

*Primary Examiner* — Jennifer A Berrios
(74) *Attorney, Agent, or Firm* — Emory Patent Group

(57) ABSTRACT

This disclosure relates to microcapsule particles for targeted delivery of drugs. In certain embodiments, the particles comprise polyelectrolyte polymers, e.g., layers of anionic polymers and cationic polymers. In certain embodiments, the particles have a fibrinogen coating. In certain embodiments, the particles contain a polysaccharide core and/or a polysaccharide coating encapsulating drugs, proteins, clotting agents, coagulation factors, or anticoagulants. In certain embodiments, this disclosure contemplates methods of using particles disclosed herein to prevent or reduce onset of or duration of bleeding. In certain embodiments, this disclosure contemplates methods of using particles disclosed herein to prevent or reduce onset of blood clotting.

2 Claims, 6 Drawing Sheets

Specification includes a Sequence Listing.

(56) References Cited

OTHER PUBLICATIONS

Rejinold et al. Dual drug encapsulated thermo-sensitive fibrinogen-graft-poly(N-isopropyl acrylamide) nanogels for breast cancer therapy, Colloids and Surfaces B: Biointerfaces 114 (2014) 209-217.
Volodkin et al. Matrix Polyelectrolyte Microcapsules: New System for Macromolecule Encapsulation, Langmuir 2004, 20, 3398-3406.
Voros et al. TPA Immobilization on Iron Oxide Nanocubes and Localized Magnetic Hyperthermia Accelerate Blood Clot Lysis, Adv. Funct. Mater. 2015, 25, 1709-1718.
Yan et al. Layer-by-layer assembly of poly(L-glutamic acid)/chitosan microcapsules for high loading and sustained release of 5-fluorouracil, European Journal of Pharmaceutics and Biopharmaceutics 78 (2011) 336-345.
Zhao et al. Assembly of multilayer microcapsules on CaCO3 particles from biocompatible polysaccharides, Journal of Biomaterials Science, Polymer Edition, 17:9, 997-1014.

\* cited by examiner

PARTICLES FOR TARGETED DELIVERY AND USES IN MANAGING BLEEDING OR BLOOD CLOTTING

CROSS-REFERENCE TO RELATED APPLICATIONS

This application is the National Stage of International Application No. PCT/US2017/015872, which claims the benefit of U.S. Provisional Application No. 62/289,642 filed Feb. 1, 2016. The entirety of each of these applications is hereby incorporated by reference for all purposes.

STATEMENT REGARDING FEDERALLY SPONSORED RESEARCH OR DEVELOPMENT

This invention was made with government support under R01 HL121264 awarded by the National Institutes of Health and W81XWH-13-1-0495 awarded by the Department of Defense. The government has certain rights in the invention.

INCORPORATION-BY-REFERENCE OF MATERIAL SUBMITTED AS A TEXT FILE VIA THE OFFICE ELECTRONIC FILING SYSTEM (EFS-WEB)

The Sequence Listing associated with this application is provided in text format in lieu of a paper copy, and is hereby incorporated by reference into the specification. The name of the text file containing the Sequence Listing is 15095US_ST25.txt. The text file is 21 KB, was created on Aug. 1, 2018, and is being submitted electronically via EFS-Web.

BACKGROUND

Mutations in the coagulation factor VIII gene result in a decreased or defective coagulation factor (fVIII) protein that gives rise to hemophilia A, which is characterized by uncontrolled bleeding. Hemophilia B is similarly associated with a genetic defect in coagulation factor IX (fIX). Treatment of hemophilia A typically entails repeated intravenous infusion of either human plasma-derived or recombinant fVIII product. Significant amounts of patients treated with fVIII replacement products develop neutralizing antibodies that render future treatment ineffective. Thus, there is a need to identify improved therapies.

Voros et al. report nanoconstructs with immobilizing tissue plasminogen activator molecules are capable of dissolving clots. Adv. Funct. Mater. 2015, 25, 1709-1718. Korin et al. report shear-activated nanotherapeutics for drug targeting to obstructed blood vessels. Science. 2012, 337 (6101):1453.

Hanafy et al. report the fabrication of homogenous CaCO$_3$ particles in assembling polyelectrolyte capsules. J. Basic Appl. Sci., 4 (2015), 60-70. It also reports that these polyelectrolyte capsules are a template for encapsulation of cargo molecules either by using co-precipitation or by loading cargo molecule after core removal. Poojari et al. report electrostatically mediated layer-by-layer assembled sorafenib nanoparticles. Colloids Surf B Biointerfaces. 2016, 143:131-8.

U.S. Pat. No. 6,391,343 reports fibrinogen-coated particles for therapeutic uses.

References cited herein are not an admission of prior art.

SUMMARY

This disclosure relates to microcapsule particles for targeted delivery of drugs. In certain embodiments, the particles comprise polyelectrolyte polymers, e.g., layers of anionic polymers and cationic polymers. In certain embodiments, the particles have a fibrinogen coating. In certain embodiments, the particles contain a polysaccharide core and/or a polysaccharide coating encapsulating drugs, proteins, clotting agents, coagulation factors, or anticoagulants. In certain embodiments, this disclosure contemplates methods of using particles disclosed herein to prevent or reduce onset of or duration of bleeding. In certain embodiments, this disclosure contemplates methods of using particles disclosed herein to prevent or reduce onset of blood clotting.

In certain embodiments, this disclosure relates to a polymer-protein microcapsule for targeted drug delivery of intravenously administered blood clot regulating drugs. In certain embodiments, the microcapsule comprises of at least four chemical regions comprising: a protein and polymer layer on the exterior of the microcapsule shell, a microcapsule shell comprised of biodegradable polyelectrolyte polymers, a separate polymer layer on the inside of the microcapsule shell, and an aqueous core containing a drug to be delivered. In certain embodiments, the drug to be delivered includes, but are not limited to, human or recombinant forms of Factor VIII, Factor VII, tissue plasminogen activator, or urokinase plasminogen activator.

In certain embodiments, this disclosure relates to particle having core comprising drugs, proteins, clotting agents, coagulation factors, or anticoagulants encapsulated inside a coating comprising: a) a cationic polymer or a polymer comprising cationic monomers; b) an anionic polymer or a polymer comprising anionic monomers; and c) an outer layer exposing fibrinogen or other protein on the outer surface.

In certain embodiments, the anionic polymer or polymer comprising the anionic monomers is under the outer layer. In certain embodiments, the cationic polymer or polymer comprising cationic monomers is poly-L-lysine. In certain embodiments, the anionic polymer or polymer comprising anionic monomers is poly-L-glutamic acid.

In certain embodiments, the particles disclosed herein further comprise a polysaccharide layer such as a dextran layer. In certain embodiments, the cationic polymer and the anionic polymer is over the polysaccharide layer.

In certain embodiments, the disclosure contemplates a particle or microcapsule for delivery of clot regulating drugs towards treating blood-clotting disorders including, but not limited to, hemophilia A, hemophilia B, severe hemorrhage, heart attack, stroke, or thrombosis.

In certain embodiments, this disclosure relates to methods of treating or preventing excessive bleeding comprising administering a particle disclosed herein to a subject in need thereof. In certain embodiments, the subject is diagnosed with hemophilia A or B or the subject is diagnosed with acquired hemophilia or thrombocytopenia.

In certain embodiments, this disclosure relates to methods of producing particle disclosed herein having core comprising a coagulation factor protein encapsulated in a coating comprising: a) mixing carbonate salt such as sodium carbonate and a calcium salt such as calcium chloride under conditions such that a calcium carbonate core is formed; b) mixing the calcium core and a polysaccharide under conditions such that a polysaccharide layer is formed over core to provide a polysaccharide layered core; c) mixing the a polysaccharide layered core with an cationic polymer under conditions such that a polymer layer comprising the cationic polymer is formed providing a cationic polymer coated core; d) mixing the cationic polymer coated core with an anionic polymer under conditions such that an polymer layer comprising the anionic polymer is formed providing a cationic polymer layer and anionic polymer layer coated core; and e) mixing the cationic polymer layer and anionic polymer layer coated core with fibrinogen under conditions such that an outer layer exposing fibrinogen on the outer surface is formed providing a fibrinogen coated particle.

In certain embodiments, the steps of both c) and d) wherein c) mixing the a polysaccharide layered core with an cationic polymer under conditions such that a polymer layer comprising the cationic polymer is formed providing a cationic polymer coated core and d) mixing the cationic polymer coated core with an anionic polymer under conditions such that an polymer layer comprising the anionic polymer is formed providing a cationic polymer layer and anionic polymer layer coated core, are repeated more than two, three, four, or five times.

In certain embodiments, the methods disclosed herein further comprise the step of exposing the fibrinogen coated particle with a water soluble chelating agent under conditions to remove the calcium ions in the core of the particle, providing a fibrinogen coated particle depleted of the calcium core, and mixing the fibrinogen coated particle depleted of the calcium core with a drug under conditions such that the coagulation factor is absorbed into the core providing a particle having core comprising a coagulation factor protein encapsulated in a coating comprising anionic and cationic polymers.

In certain embodiments, the disclosure contemplates that a drug can be co-encapsulated in the calcium carbonate core by adding it into one of the salt solutions, e.g., before mixing the carbonate salt, e.g. sodium carbonate and calcium salt, e.g. calcium chloride together. In certain embodiments, the drug is then retained in the microcapsule when the calcium carbonate core is removed In certain embodiment, this disclosure contemplates pharmaceutical compositions comprising particles disclosed herein and pharmaceutically acceptable excipient. In certain embodiments, this disclosure contemplates the production of a medicament comprising particles disclosed herein and uses for methods disclosed herein.

DETAILED DISCUSSION

Figure 1:
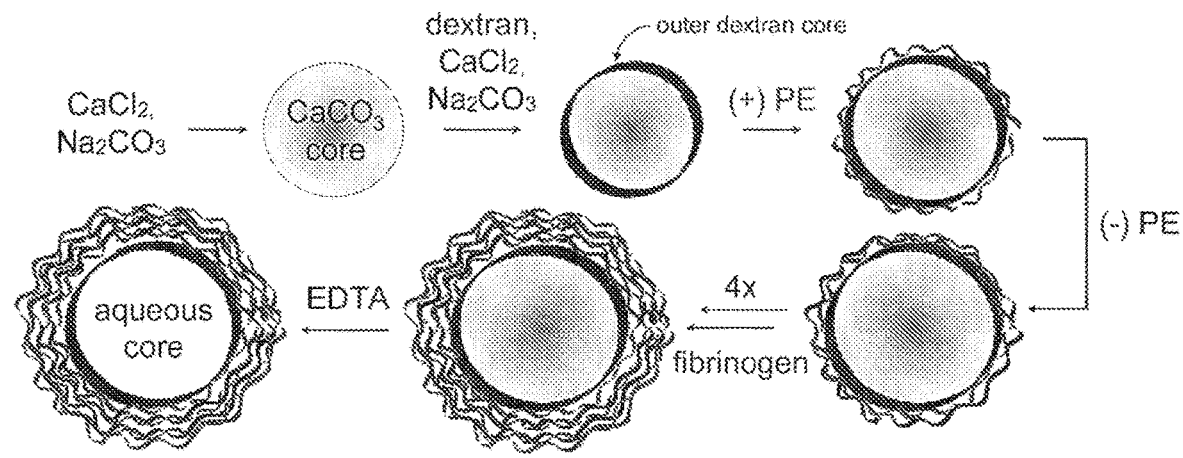
FIG. 1 illustrates polyelectrolyte microcapsule production using layer-by-layer deposition of polyelectrolytes onto calcium carbonate cores. Microcapsules have been optimized to rupture under platelet contraction and then deliver an encapsulated cargo.
Figure 2:
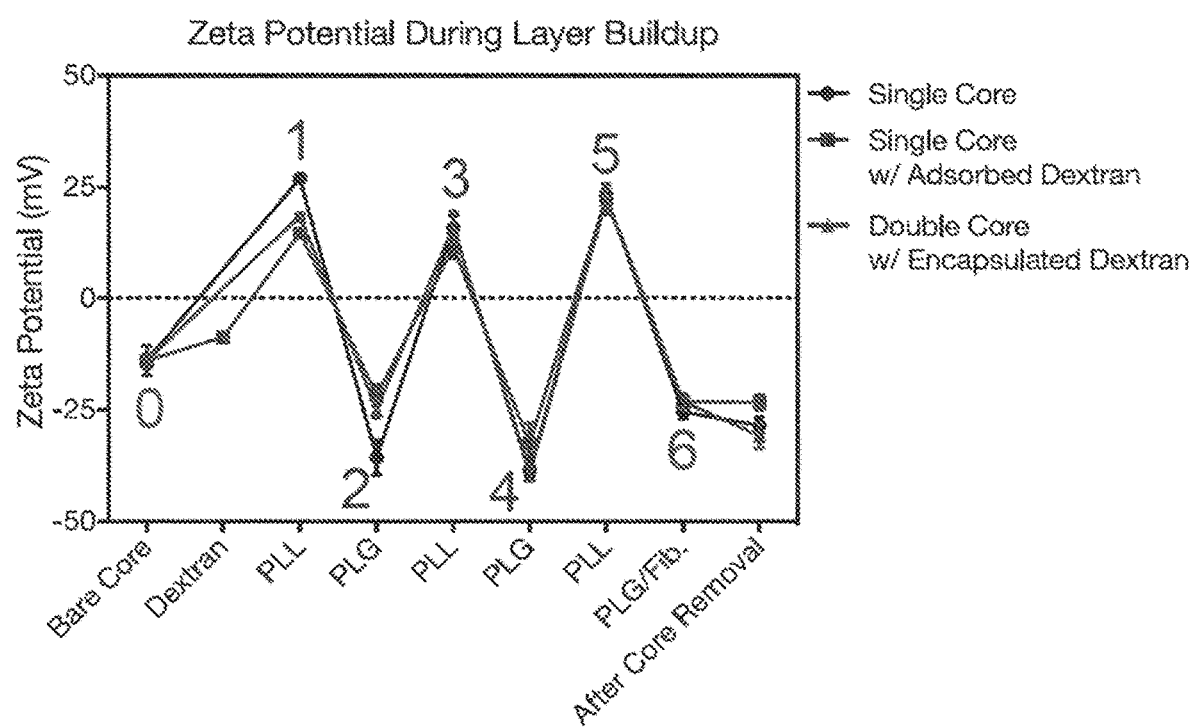
FIG. 2 shows data on the zeta potential of the microcapsule during polyelectrolyte layer deposition indicating alternating surface charge of the particles corresponding to the layer deposited, which confirms the layers were deposited.
Figure 3:
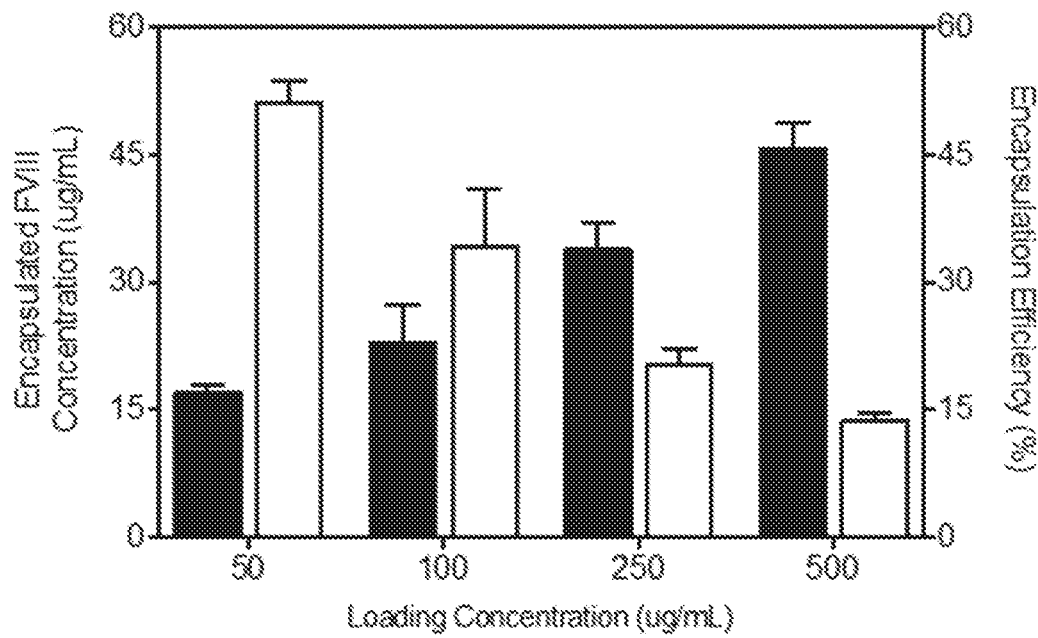
FIG. 3 shows data on microcapsule loading. FVIII is loaded into microcapsule after production and purification steps are completed.
Figure 4:
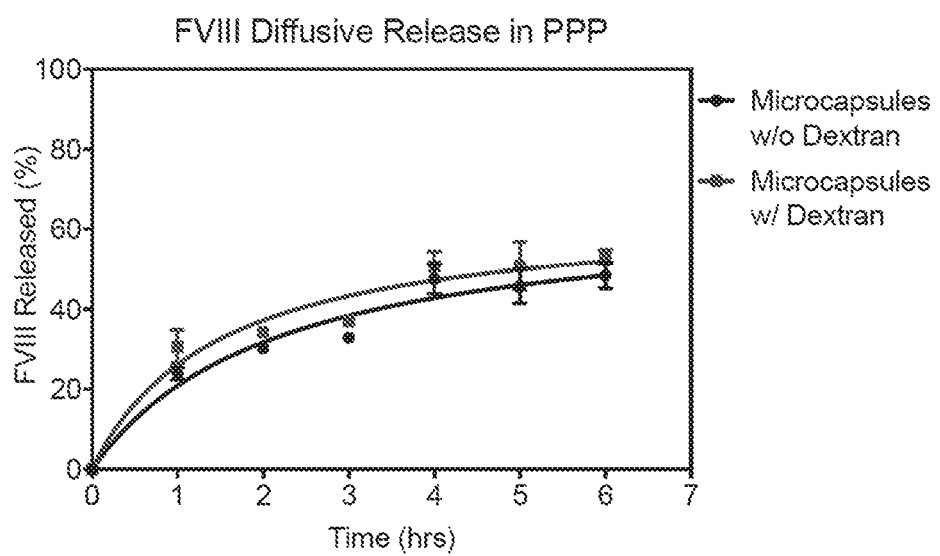
FIG. 4 shows data on the rate FVIII diffuses out of the microcapsules in platelet poor plasma (PPP). There is still about 60% of FVIII left after 3 hours, which is in the period of clot formation.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

Prior to describing the various embodiments, the following definitions are provided and should be used unless otherwise indicated.

"Cationic polymers" refer to macromolecules that are capable of bearing positive charges in solutions at acidic or near neutral pH, which can be either intrinsically present in the polymer backbone and/or in the side chains. Typical cationic polymers possess quaternary amines or primary, secondary, or tertiary functional groups that can be protonated. Examples include natural cationic polymers such as gelatin. Semi-synthetic cationic polymers such as chitosan that has a repeating amino group. The primary amino groups present on a polymer backbone provides reactive sites for a variety of side-group attachments. Other polymers and polysaccharides such as dextrin, cyclodextrin, dextran, and cellulose can be modified to contain amine groups. Other cationic polymers may be synthetic such as polyethylenimine, poly-L-lysine, poly-L-arginine, poly-L-histidine, polyamidoamine, poly(amino-co-ester)s, poly[2-(N,N-dimethylamino)ethyl methacrylate] and copolymers thereof.

"Anionic polymers" refer to macromolecules that are capable of bearing negative charges in solutions at basic or near neutral pH, which can be intrinsically present in the polymer backbone and/or in the side chains. Typical anionic polymers possess carboxylic acid, sulfate and/or phosphate groups. Examples include polyacrylate, polymethacrylate poly-L-glutamic acid, poly-L-aspartic acid, polyhydroquinone, polydibenzyl phosphate, polyvinyl sulfonate. Also contemplated are copolymers such as acrylic or methacrylic acid that has been crosslinked with a di-functional monomer (e.g., divinylbenzene).

"Polysaccharides" refer to polymers having a sugar backbone. Examples of polysaccharides include dextrans, dextrins, chitosan, pullulans, and celluloses. Dextrans refer to polysaccharides with molecular weights that are typically greater than 1,000 Dalton and have a linear backbone of repeating alpha-linked D-glucopyranosyl, such as isomaltose units. Dextrans are typically produced in bacteria. The molecular weight and spatial arrangement of dextrans depends on the microbial producing strains and cultivation conditions. There are three classes of dextran differentiated by the structural features.

As used herein, the term "biodegradable" refers to a material that when transplanted into an area of a subject, e.g., human, will be degraded my biological mechanism such that the material will not persist in the area for over a long period of time, e.g., material will be removed by the body after a couple days or a week or month(s). In certain embodiments, this disclosure contemplates that the biodegradable material will not be found at the transplanted location after one day, two days, a week, a month, six months, or a year.

As used herein, "subject" refers to any animal, preferably a human patient, livestock, or domestic pet.

As used herein, the terms "prevent" and "preventing" include the prevention of the recurrence, spread or onset. It is not intended that the present disclosure be limited to complete prevention. In some embodiments, the onset is delayed, or the severity is reduced.

As used herein, the terms "treat" and "treating" are not limited to the case where the subject (e.g. patient) is cured and the disease is eradicated. Rather, embodiments of the present disclosure also contemplate treatment that merely reduces symptoms, and/or delays disease progression.

Polymer-Protein Microcapsules for Targeted Delivery of Blood Clot Regulating Drugs Blood clot regulating drugs are administered topically for hemorrhage or intravenously for either clot promoting or clot busting treatments. Topical administration has a low risk of side effects but is ineffective in treating hemorrhage from severe trauma or non-compressible injuries. Intravenous delivery, while more effective, is done systemically, which increases the risk of side effects. These side effects include hemorrhage from clot busting drugs or heart attack and stroke from clot promoting drugs. Furthermore, patients suffering from bleeding disorders such as hemophilia A may form inhibitors to the drug, which significantly decreases the drug's efficacy.

There exists a substantial need for targeted delivery systems of clot regulating drugs administered intravenously, so as the patient is only exposed to the drug strictly at the site wherein clot regulation is needed, thereby avoiding side effects and inhibitor interactions. However, current targeted delivery technologies that have been developed are inappropriate for treating critical conditions in restrained periods. They either require external resources (magnets or lasers) to target or deliver the drug, or if they have biochemical targeting and delivery mechanisms, taking several days or even weeks to fully deliver their drug payload. A targeted delivery technology for clot regulating drugs would leverage existing biochemical and biomechanical pathways within the body to target and deliver the full dose of the drug without external equipment and within a short time frame. It is an object of the instant disclosure to address these needs.

Certain embodiments disclosed herein provides for therapeutics that are delivered systemically and become active or released at sites in blood vessels that require blood clot regulation. This is based upon using micron size capsules as vehicles that will target specific cells/tissues by interaction with naturally occurring pathways in the blood clotting mechanism such as the contractile force of platelets and their adhesion to fibrinogen.

This disclosure relates to a drug delivery approach to treat unregulated blood clotting in cases where severe blood loss and/or unwanted clotting occurs. This includes disorders such as, deep vein thrombosis, pulmonary thrombosis, Factor V Leiden Mutation, PT gene mutation, Protein C and S deficiency, Hemorrhagic Stroke, Severe Bleeding, Hemophilia A/B, von Willebrands disease.

Fibrinogen is a glycoprotein in vertebrates that helps in the formation of blood clots. Fibrinogen is a soluble, large, and complex glycoprotein, 340 kDa in size, which is converted by thrombin into fibrin during blood clot formation. During normal blood coagulation, a coagulation cascade activates the zymogen prothrombin by converting it into the serine protease thrombin. Thrombin then converts the soluble fibrinogen into insoluble fibrin strands. These strands are then cross-linked by factor XIII to form a blood clot. Factor XIIa stabilizes fibrin further by incorporation of the fibrinolysis inhibitors alpha-2-antiplasmin and TAFI (thrombin activatable fibrinolysis inhibitor, procarboxypeptidase B), and binding to several adhesive proteins of various cells.

By displaying fibrinogen on the exterior of the drug delivery vehicles, the drug-loaded vehicles will integrate into the fibrin network of the forming clot. The mechanical force of the contracting clot caused by activated platelets will rupture the vehicle and will thereby deliver the drug solely to the site of the clot.

In certain embodiments, this disclosure relates to a polymer-protein microcapsule for targeted drug delivery of intravenously administered blood clot regulating drugs. In certain embodiments, the microcapsule comprises of at least four chemical regions comprising: a protein and polymer layer on the exterior of the microcapsule shell, a microcapsule shell comprised of biodegradable polyelectrolyte polymers, a separate polymer layer on the inside of the microcapsule shell, and an aqueous core containing a drug to be delivered. In certain embodiments, the drug to be delivered includes, but are not limited to, human or recombinant forms of Factor VIII, Factor VII, tissue plasminogen activator, or urokinase plasminogen activator.

Particles disclosed herein show activity and effect in a clot-like in vitro system using static fibrin networks with a high concentration of activated platelets. Only platelets located in the fibrin network ruptured and released the drug. Drug delivery from capsules occurs only in specific clot-like structures and is controlled by contractive mechanical action of activated platelets In certain embodiments, this disclosure relates to a particle having core comprising a drug, protein, or coagulation factor encapsulated in a coating comprising: a) a cationic polymer or a polymer comprising cationic monomers; b) an anionic polymer or a polymer comprising anionic monomers; and c) an outer layer exposing fibrinogen on the outer surface.

In certain embodiments, the anionic polymer or polymer comprising the anionic monomers is under the outer layer. In certain embodiments, the coagulation factor is fVIII. In certain embodiments, the cationic polymer or polymer comprising cationic monomers is poly-L-lysine. In certain embodiments, the anionic polymer or polymer comprising anionic monomers is poly-L-glutamic acid.

In certain embodiments, the particles disclosed herein further comprise a polysaccharide layer such as a dextran layer. In certain embodiments, the cationic polymer and the anionic polymer is over the polysaccharide layer.

Figure 9:
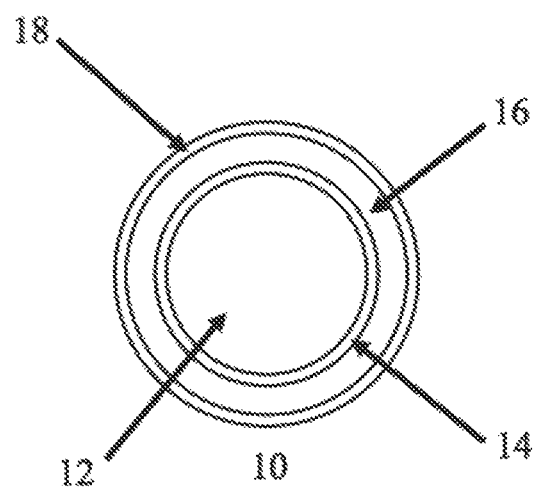
FIG. 9 shows a cross-sectional view of a microcapsule.
Figure 10:
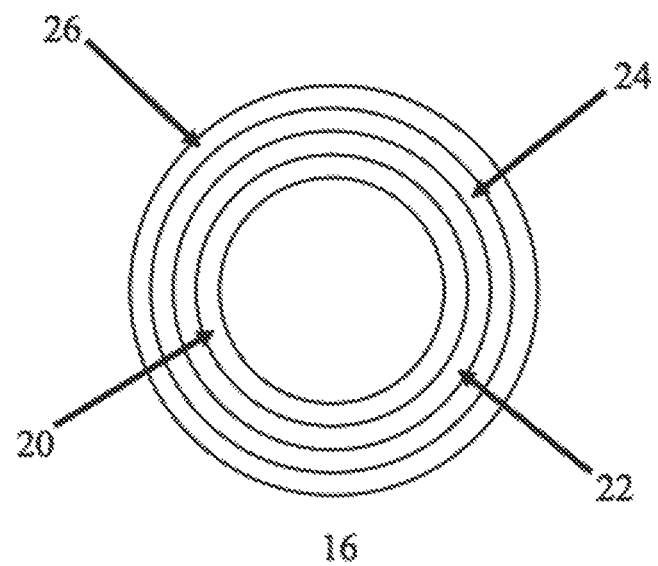
FIG. 10 shows a cross-sectional view of element 16 in FIG. 9.

In certain embodiments, this disclosure relates to a polymer-protein microcapsule for intravenous targeted drug delivery of the encapsulated drug. An illustrated embodiment is shown in FIGS. 1, 9, and 10. FIG. 9 shows a microcapsule 10 in the size range of 2 to 10 microns containing an aqueous core 12 comprising a drug. A polymer layer 14 encapsulates the core 12. The polymer layer 14 is further encapsulated by an element 16. Element 16 functions as the microcapsule shell and is comprised of several polyelectrolyte polymer layers of alternating charge. A layer 18 coats the exterior of the microcapsule shell and consists of a negatively charged protein and a negatively charged polyelectrolyte.

As illustrated in FIG. 9, the core 12 may comprise at least one drug in varying concentrations. The drug may be in a human or recombinant form of, but not limited to, Factor VIII, Factor VII, tissue plasminogen activator, or urokinase plasminogen activator. The polymer layer 14 surrounds the core 12 of the microcapsule. The layer consists of at least one of the following polymers of varying size: dextran, chitosan, PEG or PEG-PLGA.

The layer 14 functions as a barrier between the core 12 and the element 16 so that there are limited chemical or electrostatic interactions between the drug retained in the core 12 and the polymers of element 16.

The polymer layer 14 is surrounded by the element 16 of the microcapsule, which comprises several layers of polyelectrolyte polymers. The polyelectrolyte polymers are repetitively layered around layer 14 with alternating charge. The element 16 of the microcapsule comprises a minimum of 4 polyelectrolyte polymer layers, which may either be cross-linked through chemical means or held together through electrostatic interactions. The polyelectrolyte polymers may be, but are not limited to, poly-L-lysine, poly-L-glutamic acid, poly-L-arginine, poly malic acid, or dextran sulfate of various sizes.

The layer 18 of the microcapsule surrounds element 16 and functions as the exterior of the microcapsule. The layer 18 is comprised of the protein, fibrinogen, and a negatively charged polyelectrolyte in various concentration ratios. The polyelectrolyte used in layer 18 may or may not be used in element 16. The components of layer 18, that is to say the protein and negative polyelectrolyte polymer, may or may not be chemically cross-linked together. Furthermore, the components of layer 18 may or may not be chemically cross-linked to the components of element 16. The protein's biochemical activity of layer 18 is retained, such that platelets can adhere to the microcapsule exterior by binding to the protein after intravenous administration.

In FIG. 10 there is shown the element 16 from FIG. 9 in more detail illustrating the alternating layers of polyelectrolyte. In one embodiment of the invention, there may be four polyelectrolyte layers such that 20 may be comprised of the positive polyelectrolyte polymer, 22 may be comprised of the negative polyelectrolyte polymer, 24 may be comprised of the positive polyelectrolyte polymer, and 26 may be comprised of the negative polyelectrolyte polymer. The positive polyelectrolyte polymers of 20 and 24 may be the same or different polyelectrolyte polymers. The negative polyelectrolyte polymers of 22 and 26 may be the same or different polyelectrolyte polymers. Other embodiments of the invention may have more polyelectrolyte polymer layers in element 16. Each polyelectrolyte polymer layer of element 16 consists of at least one polyelectrolyte polymer of the same charge and may or may not be chemically cross-linked to the other polyelectrolyte polymer within the same layer. The polyelectrolyte polymer layers of alternating charge may or may not be chemically cross-linked to each other such that, in one embodiment of the invention, polyelectrolyte polymer layer 20 may be chemically cross-linked to polyelectrolyte polymer layer 22. This may occur for all polyelectrolyte polymer layers, some of the polyelectrolyte polymer layers, or none of them at all.

The mechanical properties of element 16 are such that the microcapsule structure will withstand forces experienced during fabrication, storage, and handling. However, the mechanical properties of element 16 are weak enough such that the microcapsule will rupture open upon contraction of platelets on the microcapsule.

The advantages of the present invention include, but are not limited to, targeted delivery and burst release of the encapsulated drug. The protein of layer 18 imparts the advantage of targeted delivery by allowing platelets to adhere to the microcapsule exterior. The adhered platelets allow the microcapsule to be directed and adhered to areas requiring blood clot regulation (target sites for the drug carried in core 12 within the microcapsule). The microcapsule is further adhered to target sites by the fibrinogen protein of layer 18, which polymerizes into the target site's fibrin network. Once the microcapsule is adhered to the target site, physical contraction of nearby platelets provides sufficient mechanical force to rupture the microcapsule shell (element 16) and release the encapsulated drug from core 12. Burst release of the drug occurs because layer 14 physically shields the drug from the electrostatic charge of element 16, allowing full exposure of the drug to the target site.

Blood Coagulation Factors

In certain embodiments, particles and microcapsules disclosed herein encapsulate a drug that can be a coagulation factor. The blood clotting system is a proteolytic cascade. Blood clotting factors are present in the plasma as a zymogen, in other words in an inactive form, which on activation undergoes proteolytic cleavage to release the active factor form the precursor molecule. The ultimate goal is to produce thrombin. Thrombin converts fibrinogen into fibrin strands. These strands are then cross-linked by factor XIII to form a blood clot.

Fibrinogen, or Factor I, has an approximate molecular weight of 340 kDa. The purification of human plasma fibrinogen by chromatography is described. See Kuyas et al., Thromb Haemost. 1990, 63(3):439-44, and Dempfle et al. Thromb Res. 1987, 46(1):19-27.

Factor X is the first molecule of the common pathway and is activated by a complex of molecules containing activated factor IX (FIXa), factor VIII, calcium, and phospholipids, which are on the platelet surface. Factor VIII is activated by thrombin, and it facilitates the activation of factor X by FIXa. Factor VIII (fVIII), contains multiple domains (A1-A2-B-ap-A3-C1-C2) and circulates in blood in an inactivated form bound to von Willebrand factor (VWF). The C2 domain is involved with fVIII binding to VWF. Thrombin cleaves fVIII causing dissociation with VWF ultimately leading to fibrin formation through factor IX (fIX).

Congenital hemophilia A is associated with genetic mutations in the fVIII gene and results in impaired clotting due to lower than normal levels of circulating fVIII. Hemophilia B is similarly associated with genetic mutations in the fIX gene.

A treatment option for a patient diagnosed with hemophilia A is the exogenous administration of recombinant fVIII sometimes referred to as fVIII replacement therapy. In some patients, this therapy can lead to the development of antibodies that bind to the administered fVIII protein. Subsequently, the fVIII-antibody bound conjugates, typically referred to as inhibitors, interfere with or retard the ability of fVIII to cause blood clotting. Inhibitory autoantibodies also sometimes occur spontaneously in a subject that is not genetically at risk of having hemophilia, termed acquired hemophilia. Inhibitory antibodies assays are typically performed prior to exogenous fVIII treatment in order to determine whether the anti-coagulant therapy will be effective.

A "Bethesda assay" has historically been used to quantitate the inhibitory strength the concentration of factor VIII binding antibodies. In the assay, serial dilutions of plasma from a patient, e.g., prior to having surgery, are prepared and each dilution is mixed with an equal volume of normal plasma as a source of fVIII. After incubating for a couple hours, the activities of factor VIII in each of the diluted mixtures are measured. Having antibody inhibitor concentrations that prevent factor VIII clotting activity after multiple repeated dilutions indicates a heightened risk of uncontrolled bleeding. Patients with inhibitor titers after about ten dilutions are felt to be unlikely to respond to exogenous fVIII infusions to stop bleeding. A Bethesda titer is defined as the reciprocal of the dilution that results in 50% inhibition of FVIII activity present in normal human plasma. A Bethesda titer greater than 10 is considered the threshold of response to FVIII replacement therapy. Thus, in certain embodiments, this disclosure contemplates that a subject to receive administrations of pharmaceutical compositions comprising particles disclosed herein is diagnosed with a Bethesda titer of greater than 5, 6, 7, 8, 9, or 10.

In blood plasma, Factor VIII is usually complexed with another plasma protein, von Willebrand factor (vWF), which is present in plasma in a large molar excess to Factor VIII and is believed to protect Factor VIII from premature degradation. Another circulating plasma protein, albumin, may also play a role in stabilizing Factor VIII in vivo. Factor VIII preparations use of albumin and/or vWF to stabilize Factor VIII during the manufacturing process and during storage. In certain embodiments, this disclosure contemplates particles comprising Factor VIII in the core in combination with albumin and/or vWF.

FVIII is a large glycoprotein containing the domain structure A1-A2-B-activation peptide (ap)-A3-C1-C2. Gitschier et al., Nature, 1984, 312, 326-330. Factor VIII domain boundaries refer to the human fVIII amino acid sequence numbering as follows; residues 1-19 (Signal Sequence), 20-391 (A1), 392-759 (A2), 760-1667 (B), 1668-1708 (ap), 1709-2038 (A3), 2039-2191 (C1) and 2192-2351 (C2). Gitschier et al., Nature, 1984, 312, 326-330. (SEQ ID NO: 1):

```
  1 MQIELSTCFF LCLLRFCFSA TRRYYLGAVE LSWDYMQSDL GELPVDARFP PRVPKSFPFN

61 TSVVYKKTLF VEFTDHLFNI AKPRPPWMGL LGPTIQAEVY DTVVITLKNM ASHPVSLHAV

GVSYWKASEG AEYDDQTSQR EKEDDKVFPG GSHTYVWQVL KENGPMASDP LCLTYSYLSH

VDLVKDLNSG LIGALLVCRE GSLAKEKTQT LHKFILLFAV FDEGKSWHSE TKNSLMQDRD

AASARAWPKM HTVNGYVNRS LPGLIGCHRK SVYWHVIGMG TTPEVHSIFL EGHTFLVRNH

301 RQASLEISPI TFLTAQTLLM DLGQFLLFCH ISSHQHDGME AYVKVDSCPE EPQLRMKNNE

EAEDYDDDLT DSEMDVVRFD DDNSPSFIQI RSVAKKHPKT WVHYIAAEEE DWDYAPLVLA

421 PDDRSYKSQY LNNGPQRIGR KYKKVRFMAY TDETFKTREA IQHESGILGP LLYGEVGDTL

LIIFKNQASR PYNIYPHGIT DVRPLYSRRL PKGVKHLKDF PILPGEIFKY KWTVTVEDGP
```

-continued

```
           TKSDPRCLTR  YYSSFVNMER  DLASGLIGPL  LICYKESVDQ  RGNQIMSDKR  NVILFSVFDE

NRSWYLTENI  QRFLPNPAGV  QLEDPEFQAS  NIMHSINGYV  FDSLQLSVCL  HEVAYWYILS

IGAQTDFLSV  FFSGYTFKHK  MVYEDTLTLF  PFSGETVFMS  MENPGLWILG  CHNSDFRNRG

MTALLKVSSC  DKNTGDYYED  SYEDISAYLL  SKNNAIEPRS  FSQNSRHPST  RQKQFNATTI

781  PENDIEKTDP  WFAHRTPMPK  IQNVSSSDLL  MLLRQSPTPH  GLSLSDLQEA  KYETFSDDPS

PGAIDSNNSL  SEMTHFRPQL  HHSGDMVFTP  ESGLQLRLNE  KLGTTAATEL  KKLDFKVSST

SNNLISTIPS  DNLAAGTDNT  SSLGPPSMPV  HYDSQLDTTL  FGKKSSPLTE  SGGPLSLSEE

NNDSKLLESG  LMNSQESSWG  KNVSSTESGR  LFKGKRAHGP  ALLTKDNALF  KVSISLLKTN

1021  KTSNNSATNR  KTHIDGPSLL  IENSPSVWQN  ILESDTEFKK  VTPLIHDRML  MDKNATALRL

NHMSNKTTSS  KNMEMVQQKK  EGPIPPDAQN  PDMSFFKMLF  LPESARWIQR  THGKNSLNSG

QGPSPKQLVS  LGPEKSVEGQ  NFLSEKNKVV  VGKGEFTKDV  GLKEMVFPSS  RNLFLTNLDN

1201  LHENNTHNQE  KKIQEEIEKK  ETLIQENVVL  PQIHTVTGTK  NFMKNLFLLS  TRQNVEGSYD

GAYAPVLQDF  RSLNDSTNRT  KKHTAHFSKK  GEEENLEGLG  NQTKQIVEKY  ACTTRISPNT

SQQNFVTQRS  KRALKQFRLP  LEETELEKRI  IVDDTSTQWS  KNMKHLTPST  LTQIDYNEKE

1381  KGAITQSPLS  DCLTRSHSIP  QANRSPLPIA  KVSSFPSIRP  IYLTRVLFQD  NSSHLPAASY

RKKDSGVQES  SHFLQGAKKN  NLSLAILTLE  MTGDQREVGS  LGTSATNSVT  YKKVENTVLP

KPDLPKTSGK  VELLPKVHIY  QKDLFPTETS  NGSPGHLDLV  EGSLLQGTEG  AIKWNEANRP

GKVPFLRVAT  ESSAKTPSKL  LDPLAWDNHY  GTQIPKEEWK  SQEKSPEKTA  FKKKDTILSL

NACESNHAIA  AINEGQNKPE  IEVTWAKQGR  TERLCSQNPP  VLKRHQREIT  RTTLQSDQEE

IDYDDTISVE  MKKEDFDIYD  EDENQSPRSF  QKKTRHYFIA  AVERLWDYGM  SSSPHVLRNR

AQSGSVPQFK  KVVFQEFTDG  SFTQPLYRGE  LNEHLGLLGP  YIRAEVEDNI  MVTFRNQASR

PYSFYSSLIS  YEEDQRQGAE  PRKNFVKPNE  TKTYFWKVQH  HMAPTKDEFD  CKAWAYFSDV

DLEKDVHSGL  IGPLLVCHTN  TLNPAHGRQV  TVQEFALFFT  IFDETKSWYF  TENMERNCRA

1921  PCNIQMEDPT  FKENYRFHAI  NGYIMDTLPG  LVMAQDQRIR  WYLLSMGSNE  NIHSIHFSGH

VFTVRKKEEY  KMALYNLYPG  VFETVEMLPS  KAGIWRVECL  IGEHLHAGMS  TLFLVYSNKC

QTPLGMASGH  IRDFQITASG  QYGQWAPKLA  RLHYSGSINA  WSTKEPFSWI  KVDLLAPMII

HGIKTQGARQ  KFSSLYISQF  IIMYSLDGKK  WQTYRGNSTG  TLMVFFGNVD  SSGIKHNIFN

2161  PPIIARYIRL  HPTHYSIRST  LRMELMGCDL  NSCSMPLGME  SKAISDAQIT  ASSYFTNMFA

TWSPSKARLH  LQGRSNAWRP  QVNNPKEWLQ  VDFQKTMKVT  GVTTQGVKSL  LTSMYVKEFL

ISSSQDGHQW  TLFFQNGKVK  VFQGNQDSFT  PVVNSLDPPL  LTRYLRIHPQ  SWVHQIALRM

2341  EVLGCEAQDL  Y
```

Before cell secretion, fVIII is cleaved at the B/ap-A3 domain junction into A1-A2-B (heavy chain) and ap-A3-C1-C2 (light chain) subunits. fVIII circulates in the plasma as an inactive heavy chain/light chain heterodimeric procofactor that is non-covalently bound to von Willebrand factor. Proteolytic activation of fVIII by thrombin results from cleavages at Arg-372 between the A1 and A2 domains, Arg-740 between the A2 and B domains, and Arg-1689 between the ap and A3 domains. During this process, the covalent linkage between the A1 and A2 domains is lost, and the B domain and 41-residue ap are released, producing a heterotrimeric, A1/A2/A3-C1-C2 subunit structure. See Doering et al. J Biol Chem. 2004, 279(8):6546-52. A number of functional B-domain-deleted recombinant factor VIII proteins containing a linker with recognition sequence for PACE/furin processing sequence, RHQR (SEQ ID NO: 2), substituted for the B-domain are known. See Sandberg et al. Thromb Haemost. 2001, 85(1):93-100 and Brown et al., Mol Ther Methods Clin Dev. 2014, 1:14036.

Methods of Use

In certain embodiments, this disclosure contemplates methods of using particles disclosed herein to prevent or reduce onset of or duration of bleeding. In certain embodiments, this disclosure contemplates methods of using particles disclosed herein to prevent or reduce onset of blood clotting. In certain embodiments, the disclosure contemplates a particle or microcapsule for delivery of clot regulating drugs towards treating or preventing blood-clotting disorders including, but not limited to, hemophilia A, hemophilia B, severe hemorrhage, heart attack, stroke, or thrombosis.

In certain embodiments, the disclosure relates to methods of inducing blood clotting comprising administering an effective amount of a particle as disclosed herein to a subject in need thereof. In certain embodiments, the subject is diagnosed with hemophilia A or B or acquired hemophilia and/or unlikely to respond to exogenous fVIII infusions.

In certain embodiments, the methods are provided to increase the speed or strength of blood clot formation. In certain embodiments, this disclosure contemplates methods of using particles disclosed herein to prevent or reduce onset of or duration of bleeding.

In certain embodiments, the methods include controlling and/or preventing bleeding episodes in adults and children (0-16 years) with hemophilia A. In certain embodiments, the methods include perioperative management, e.g., administration prior to surgery or anesthesia, in adults and children (0-16 years) with hemophilia A.

In certain embodiments, the methods include routine prophylaxis to prevent or reduce the frequency of bleeding episodes in adults and children (0-16 years) with hemophilia A. For prevention of bleeding episodes, doses between 20 to 40 International Units of Factor VIII per kg body weight every other day (3 to 4 times weekly) may be utilized. Alternatively, an every third day dosing regimen targeted to maintain FVIII trough levels ≥1% may be employed. In certain embodiments, the methods contemplate a subject under the age of 6, is administered doses of 25 to 50 IU of Factor VIII per kg body weight 3 to 4 times weekly.

In certain embodiments, this disclosure contemplates therapeutic methods comprising the step of administering (e.g., to inject or infuse) fibrinogen coated particles disclosed herein intravenously for the purpose of decreasing bleeding time in thrombocytopenic subject. Thrombocytopenic subjects lack a sufficient concentration of platelets that are essential cellular elements responsible for hemostasis. In a thrombocytopenic animal, the number of platelets is not sufficient to form a plug quickly. As a result, it takes a much longer time for bleeding to stop. It is anticipated that in patients about to undergo surgery with major blood loss, or in trauma patients such as soldiers wounded in the battlefield, even though they have a "normal" platelet count, an augmentation of the number of particles will decrease blood loss and lead to shortened surgical time. Subjects at risk of thrombocytopenic include those with aplastic anemia, cancer in the bone marrow, such as leukemia, cirrhosis (liver scarring), folate deficiency, myelodysplastic syndrome and a vitamin B12 deficiency.

In certain embodiments, the methods are provided to prevent, decrease the speed, reduce or weaken blood clot formation. In certain embodiments, the disclosure relates to methods of preventing blood clotting comprising administering an effective amount of a particle disclosed herein carrying or encapsulating or comprising immobilizing tissue plasminogen activator molecules (tPA) and/or other anticlotting agent on the interior of the particle, e.g., warfarin (coumadin), acenocoumarol, phenprocoumon, atromentin, phenindione, a heparin, heparin tetrasaccharide, pentosan polysulfate, phosphomannopentanose sulfate, factor IIa (dabigatran) and factor Xa (rivaroxaban, apixaban and edoxaban), to a subject in need thereof.

Pharmaceutical Compositions

In certain embodiment, this disclosure contemplates pharmaceutical compositions comprising particles disclosed herein and pharmaceutically acceptable excipient. In certain embodiments, this disclosure contemplates the production of a medicament comprising particles disclosed herein and uses for methods disclosed herein.

Pharmaceutical compositions typically comprise an effective amount of particles and a suitable pharmaceutical acceptable carrier. The preparations can be prepared in a manner known per se, which usually involves mixing the particles according to the disclosure with the one or more pharmaceutically acceptable carriers, and, if desired, in combination with other pharmaceutical active compounds, when necessary under aseptic conditions. Reference is made to U.S. Pat. Nos. 6,372,778, 6,369,086, 6,369,087 and 6,372,733 and the further references mentioned above, as well as to the standard handbooks, such as the latest edition of Remington's Pharmaceutical Sciences.

In certain embodiments, the disclosure relates to pharmaceutical compositions comprising particles disclosed herein and a pharmaceutically acceptable excipient. In certain embodiments, the composition is a pill or in a capsule or the composition is an aqueous buffer, e.g., a pH between 6 and 8. In certain embodiments, the pharmaceutically acceptable excipient is selected from a filler, glidant, binder, disintegrant, lubricant, and saccharide. Optionally, the pharmaceutical composition further comprises a second clotting agent such as aminocaproic acid (ε-aminocaproic acid), tranexamic acid, fibrinogen, and vitamin K.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents solvents or vehicles include water, ethanol, polyols (propylene glycol, polyethylene glycol, glycerol, and the like), suitable mixtures thereof, vegetable (such as olive oil, sesame oil and viscoleo) and injectable organic esters such as ethyl oleate.

Prevention of the action of microorganisms may be controlled by addition of any of various antibacterial and antifungal agents, example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders and granules. In such solid dosage forms, the particles may be admixed with at least one inert customary excipient (or carrier) such as sodium citrate or dicalcium phosphate or: (a) fillers or extenders, as for example, starches, lactose, sucrose, glucose, mannitol and silicic acid, (b) binders, as for example, carboxymethylcellulose, alginates, gelatin, polyvinylpyrrolidone, sucrose, and acacia, (c) humectants, as for example, glycerol (d) disintegrating agents, as for example, agar-agar, calcium carbonate, potato or tapioca starch, alginic acid, certain complex silicates, and sodium carbonate, (e) solution retarders, as for example paraffin, (f) absorption accelerators, as for example, quaternary ammonium compounds, (g) wetting agents, as for example cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Liquid dosage forms for oral administration include pharmaceutically acceptable emulsions, solutions, suspensions, syrups, and elixirs. In addition to the particles, the liquid dosage forms may contain inert diluents commonly used in the art, such as water or other solvents, solubilizing agents and emulsifiers, for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, viscoleo, castor oil and sesame oil, glycerol, tetrahydrofurfuryl alcohol, polyethyleneglycols and fatty acid esters of sorbitan or mixtures of these substances, and the like.

In certain embodiments, production processes are contemplated which two components, d particles disclosed herein and a pharmaceutical carrier, are provided already in a combined dry form ready to be reconstituted together. In other embodiments, it is contemplated that particles disclosed herein and a pharmaceutical carrier are admixed to provide a pharmaceutical composition.

Providing a pharmaceutic composition is possible in a one-step process, simply by adding a suitable pharmaceutically acceptable diluent to the composition in a container. In certain embodiments, the container is preferably a syringe for administering the reconstituted pharmaceutical composition after contact with the diluent. In certain embodiments, the coated particles can be filled into a syringe, and the syringe can then be closed with the stopper. A diluent is used in an amount to achieve the desired end-concentration. The pharmaceutical composition may contain other useful component, such as ions, buffers, excipients, stabilizers, etc.

A "dry" pharmaceutical composition typically has only a residual content of moisture, which may approximately correspond to the moisture content of comparable commercial products, for example, has about 12% moisture as a dry product. Usually, the dry pharmaceutical composition according to the present invention has a residual moisture content preferably below 10% moisture, more preferred below 5% moisture, especially below 1% moisture. The pharmaceutical composition can also have lower moisture content, e.g. 0.1% or even below. In certain embodiments, the pharmaceutical composition is provided in dry in order to prevent degradation and enable storage stability.

A container can be any container suitable for housing (and storing) pharmaceutically compositions such as syringes, vials, tubes, etc. The pharmaceutical composition may then preferably be applied via specific needles of the syringe or via suitable catheters. A typical diluent comprises water for injection, and NaCl (preferably 50 to 150 mM, especially 110 mM), $CaCl_2$) (preferably 10 to 80 mM, especially 40 mM), human albumin (preferably up to 2% w/w, especially 0.5% w/w), sodium acetate (preferably 0 to 50 mM, especially 20 mM) and mannitol (preferably up to 10% w/w, especially 2% w/w). Preferably, the diluent can also include a buffer or buffer system so as to buffer the pH of the reconstituted dry composition, preferably at a pH of 6.2 to 7.5, especially at pH of 6.9 to 7.1.

In certain embodiments, the diluent is provided in a separate container. This can preferably be a syringe. The diluent in the syringe can then easily be applied to the container for reconstitution of the dry compositions. If the container is also a syringe, both syringes can be finished together in a pack. It is therefore preferred to provide the dry compositions in a syringe, which is finished with a diluent syringe with a pharmaceutically acceptable diluent for reconstituting, said dry and stable composition.

In certain embodiments, this disclosure contemplates a kit comprising a pharmaceutical composition disclosed herein and a container with a suitable diluent. Further components of the kit may be instructions for use, administration means, such as syringes, catheters, brushes, etc. (if the compositions are not already provided in the administration means) or other components necessary for use in medical (surgical) practice, such as substitute needles or catheters, extra vials or further wound cover means. In certain embodiments, the kit comprises a syringe housing the dry and stable hemostatic composition and a syringe containing the diluent (or provided to take up the diluent from another diluent container).

EXAMPLES

Microcapsule Fabrication

The production of microcapsules is illustrated in FIG. 1. Calcium carbonate cores used to template the fabrication of microcapsules by mixing equal volumes of 0.3 M calcium chloride and 0.3 M sodium carbonate for 30 seconds. The mixture was left to stand for 10 minutes, then washed with DI water 3*x* and dried over vacuum. For cores with an additional calcium carbonate layer loaded with dextran, the above-fabricated cores were dissolved in DI water at 80 mg/mL. To the stirring core solution, 1 mL of 0.3 M sodium carbonate and 1 mL of 0.3 M calcium chloride with 5 mg dextran or dextran-FITC were simultaneously added. Stir was continued for 30 seconds, and then the solution was left to stand for 10 minutes. Cores were washed 3 times with DI water and dried under vacuum.

To make the microcapsules, 2 mg/mL solutions of poly-l-lysine (PLL) and poly-l-glutamic acid (PLG) were made with 0.5 M NaCl, pH 6.25. Polyelectrolyte layers were deposited onto the cores with alternating charge in a layer-by-layer fashion. In brief, a 2% w/v solution of cores was dispersed in the PLL solution for 10 minutes. The cores were then pelleted at 200 g for 5 minutes and washed 3 times with 0.5 M NaCl pH 6.25 before the next layer was deposited. To deposit the fibrinogen on the surface of the microcapsule, a 1:1 solution of human fibrinogen and PLG was used for deposition of the last polyelectrolyte layer. When the desired number of layers was deposited, the cores were dispersed in a 0.2 M EDTA solution at pH 6.25 for 30 minutes to remove the calcium carbonate. The microcapsules were then washed and pelleted several times with 5 mM MES pH 6.25. Microcapsules were then stored at 4° C. until use.

To load FVIII into the microcapsules, the appropriate concentration of FVIII was incubated with the microcapsules at a particle density of 1 million/mL for 1 hour in pH 6.25 MES buffer. The microcapsules were then washed and pelleted several times to remove any unloaded FVIII.

Zeta Potential

Zeta potential of cores during PEM synthesis was measured with a Malvern Zetasizer Nano Series (Malvern, UK). Samples were diluted with DI water at a 1:9 ratio. Each sample was measured 3 times at 20 runs for each measurement. See FIG. 2.

FVIII Diffusion

FIG. 3 is a graph concerning loading optimization of FVIII into the microcapsule. Data on FVIII diffusive release is shown in FIG. 4. Fluorescent measurements were taken on a Cytation 5 Imaging Reader by BioTek (Winooski, Vt.) and were conducted in triplicate. Loading of FVIII-RBITC in calcium carbonate cores was calculated by measuring the fluorescence intensity of FVIII-RBITC in the wash fraction during core fabrication.

Experiments measuring the diffusive release of FVIII-RBITC out of capsules were conducted in PPP at 37° C. and under 40 rpm agitation. At appropriate time points, capsules were pelleted and an aliquot of the supernatant was removed to measure diffusive release of FVIII-RBITC. A PPP aliquot of the same volume was added back to the capsule solution to preserve sample volume. Fluorescence intensity of the supernatant was measured and compared to a standard curve to calculate concentration of released FVIII-RBITC in the supernatant.

Static Fibrin Clots

Static fibrin clot experiments were fabricated by mixing fibrinogen, 1 U/mL thrombin, 10 mM calcium, washed platelets stained with Cell Mask Deep Red, and microcapsules on a glass slides treated with sigmacote. Clots were formed at 37° C. and 60% humidity and imaged via confocal laser scanning microscopy using a Zeiss LSM 710 NLO system (Thornwood, N.Y.).

Clotting on Collagen/TF Patch in Microfluidic Channels

Figure 5:
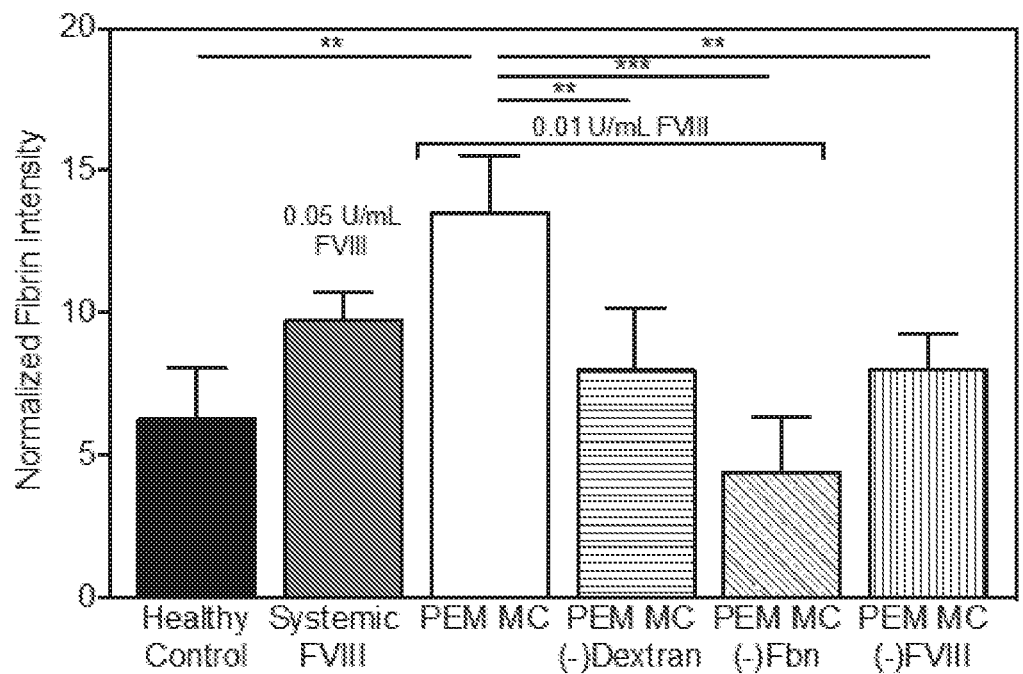
FIG. 5 shows data on fibrin formation in an in vitro blood vessel injury model. Shown are the normalized intensities of fibrin on the collagen/tissue factor patch, which is a downstream indicator of the extent of clot formation, and FVIII efficacy on the patch. All conditions used healthy patient blood to test components of the microcapsule structure. The graph shows that there is an increase in normalized fibrin intensity when FVIII is delivered in the microcapsules compared to systemic delivery. PEM MC refers to the polyelectrolyte microcapsule. Fbn refers to fibrinogen.
Figure 6:
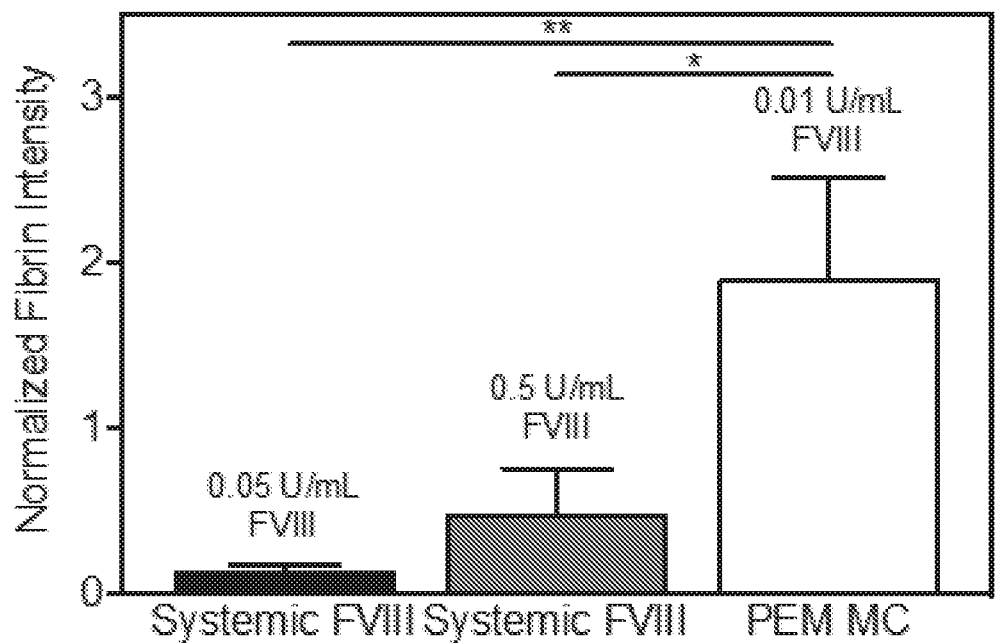
FIG. 6 shows data fibrin formation in an in vitro blood vessel injury model with FVIII inhibitory antibody, MAb 2-76, to simulate hemophilia with inhibitors. The data indicates that there is an increase in normalized fibrin intensity when FVIII is delivered in the microcapsules compared to systemic delivery. PEM MC refers to the polyelectrolyte microcapsule.
Figure 7:
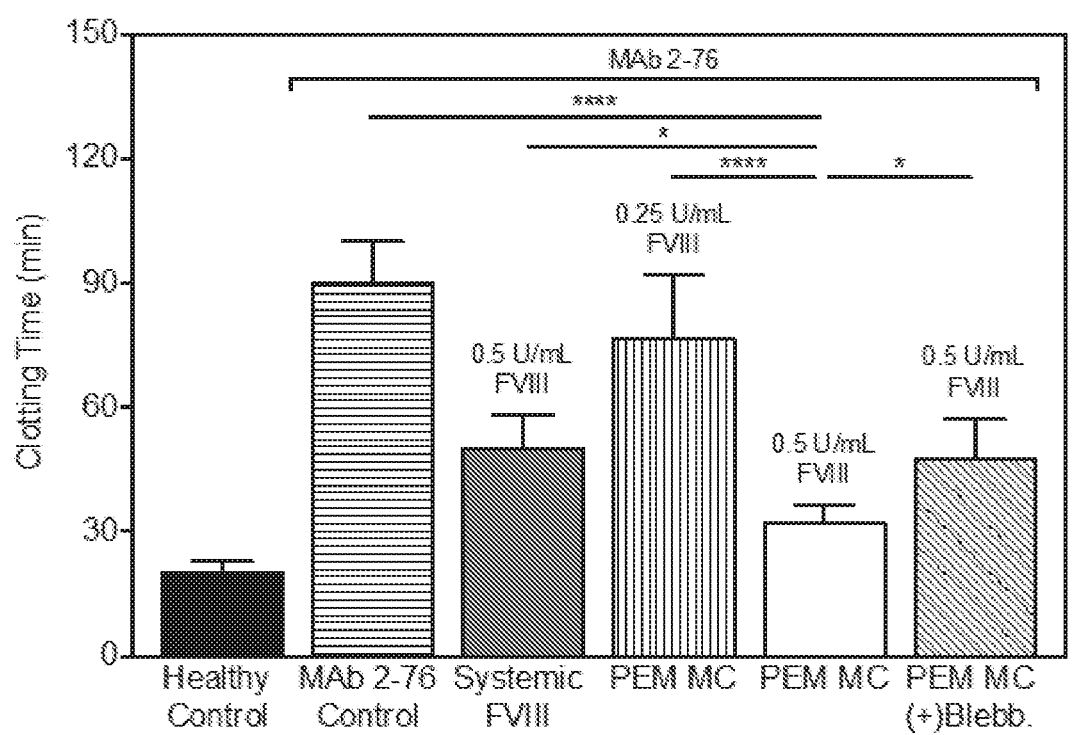
FIG. 7 shows data on the time required to form a blood clot for various conditions. This set of experiments Advate (recombinant FVIII) is used as the source. When Advate is delivered in the microcapsules compared to systemically, there is a statistically significant decrease in clotting time. Furthermore, when blebbistatin is added, which inhibits platelet contraction; there is an increase in clotting time suggesting platelet contraction is necessary for FVIII release.
Figure 8A:
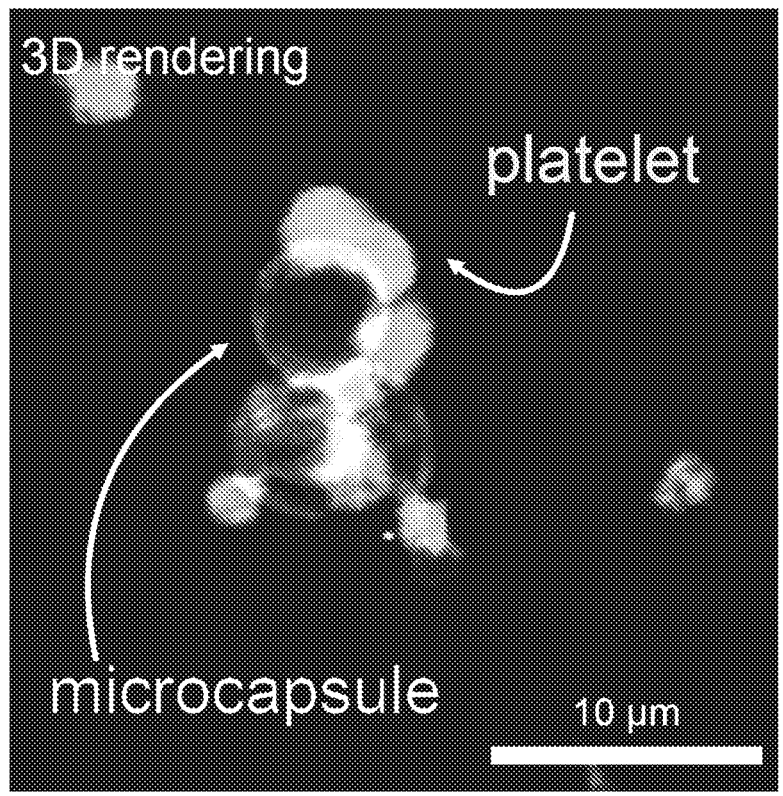
FIG. 8A shows an image taken with a confocal microscope. Static clot-like experiments were performed using fibrinogen, washed platelets, and microcapsules loaded with a model cargo. Microcapsule morphology was monitored when exposed to activated platelets in a fibrin network. Calcium, magnesium, and thrombin were added to initiate fibrin formation and platelet activation.
Figure 8B:
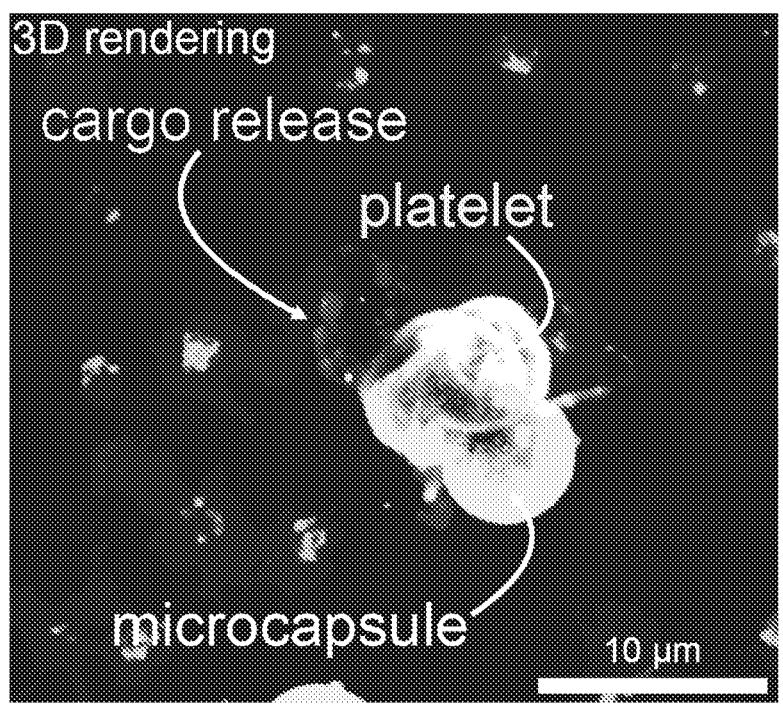
FIG. 8B shows an image taken with a confocal microscope indicating that platelet contractile forces are strong enough to cause microcapsule rupture and release of a model cargo. These microcapsules have been optimized to rupture under platelet contraction and then deliver an encapsulated cargo.

Data for clotting studies are shown in FIGS. 5-7. To form the perpendicular collagen/TF patch in the center of the microfluidic channel, a PDMS-based straight channel with a width of 2 µm was bonded to a clean glass slide. Collagen (0.5 mg/mL) and TF (4 nM) in 0.01 M acetic acid was perfused through the channel and incubated at room temperature for 1.5 hours. The PDMS straight-channel was removed and slide was rinsed with DI water and dried with nitrogen. A straight channel was cut into the silicone transfer tape with a width of 1.2 µm. One side of the tape was adhered to a piece of clean PDMS. The remaining side was then adhered to the glass slide containing the collagen/TF strip. The tape was aligned such that the collagen/TF strip was perpendicular to and in the middle of the tape straight channel. After adherence to the coverslip, the glass was blocked with 5% BSA for 1 hour.

WB was perfused at 5 µL/min for 10 minutes followed by PPP at 5 µL/min for 30 minutes. Both WB and PPP was recalcified to 5 mM and contained 2 mM Mg, CD41a-APC (platelet specific antibody), 59D8-AF488 (fibrin specific antibody), and experiment condition (PBS, systemic FVIII, or FVIII in microcapsules). For experiments mimicking hemophilia with inhibitory antibodies, MAb 2-76 was added to both WB and PPP. Samples were kept at the same total volume. They also contained the same WB or PPP volumes.

The collagen patch was monitored over time via confocal laser scanning microscopy using a Zeiss LSM 700 system (Thornwood, N.Y.). Videos were constructed by taking images every 10 seconds. Tile scans were taken of the entire patch after the experiment ended and used to measure fluorescence intensity of fibrin, platelets, and FVIII on the patch via Image J.

Clot Formation Time

For well plate clots citrated whole blood was mixed with MAb 2-76 for 30 minutes followed by addition of 5 mM Ca, 2 mM Mg, and 12 pM TF. Advate or microcapsules loaded with Advate were added at the appropriate concentration. Samples (50 uL) were loaded into wells and washed with PBS to remove soluble blood products at appropriate time points until the wash solution was clear. Samples were considered clotted when the clot covered the bottom of well and remained unchanged between time points.

The invention claimed is:

1. A particle having a core comprising factor VIII encapsulated in a coating comprising:

a) a cationic polymer layer, wherein the cationic polymer layer comprises poly-L-lysine;

b) an anionic polymer layer, wherein the anionic polymer layer comprises poly-L-glutamic acid, and the cationic polymer layer is over a polysaccharide layer;

c) an outer layer exposing fibrinogen on the outer surface, wherein the anionic polymer layer is under the outer layer; and wherein the polysaccharide is a dextran.

2. A pharmaceutical composition comprising a particle of claim 1 and a pharmaceutically acceptable excipient.

* * * * *

SEQUENCE LISTING

```
<160> NUMBER OF SEQ ID NOS: 2

<210> SEQ ID NO 1
<211> LENGTH: 2351
<212> TYPE: PRT
<213> ORGANISM: Homo sapiens

<400> SEQUENCE: 1

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
                20                  25                  30

Trp Asp Tyr Met Gln Ser Asp Leu Gly Glu Leu Pro Val Asp Ala Arg
            35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175
```

```
Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590
```

-continued

```
Ile Leu Phe Ser Val Phe Asp Glu Asn Arg Ser Trp Tyr Leu Thr Glu
            595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Ser Arg His Pro
        755                 760                 765

Ser Thr Arg Gln Lys Gln Phe Asn Ala Thr Thr Ile Pro Glu Asn Asp
    770                 775                 780

Ile Glu Lys Thr Asp Pro Trp Phe Ala His Arg Thr Pro Met Pro Lys
785                 790                 795                 800

Ile Gln Asn Val Ser Ser Ser Asp Leu Leu Met Leu Leu Arg Gln Ser
                805                 810                 815

Pro Thr Pro His Gly Leu Ser Leu Ser Asp Leu Gln Glu Ala Lys Tyr
            820                 825                 830

Glu Thr Phe Ser Asp Asp Pro Ser Pro Gly Ala Ile Asp Ser Asn Asn
        835                 840                 845

Ser Leu Ser Glu Met Thr His Phe Arg Pro Gln Leu His His Ser Gly
    850                 855                 860

Asp Met Val Phe Thr Pro Glu Ser Gly Leu Gln Leu Arg Leu Asn Glu
865                 870                 875                 880

Lys Leu Gly Thr Thr Ala Ala Thr Glu Leu Lys Lys Leu Asp Phe Lys
                885                 890                 895

Val Ser Ser Thr Ser Asn Asn Leu Ile Ser Thr Ile Pro Ser Asp Asn
            900                 905                 910

Leu Ala Ala Gly Thr Asp Asn Thr Ser Ser Leu Gly Pro Pro Ser Met
        915                 920                 925

Pro Val His Tyr Asp Ser Gln Leu Asp Thr Thr Leu Phe Gly Lys Lys
    930                 935                 940

Ser Ser Pro Leu Thr Glu Ser Gly Gly Pro Leu Ser Leu Ser Glu Glu
945                 950                 955                 960

Asn Asn Asp Ser Lys Leu Leu Glu Ser Gly Leu Met Asn Ser Gln Glu
                965                 970                 975

Ser Ser Trp Gly Lys Asn Val Ser Ser Thr Glu Ser Gly Arg Leu Phe
            980                 985                 990

Lys Gly Lys Arg Ala His Gly Pro Ala Leu Leu Thr Lys Asp Asn Ala
        995                 1000                1005

Leu Phe Lys Val Ser Ile Ser Leu Leu Lys Thr Asn Lys Thr Ser
```

```
            1010                1015                1020

Asn Asn Ser Ala Thr Asn Arg Lys Thr His Ile Asp Gly Pro Ser
    1025                1030                1035

Leu Leu Ile Glu Asn Ser Pro Ser Val Trp Gln Asn Ile Leu Glu
    1040                1045                1050

Ser Asp Thr Glu Phe Lys Lys Val Thr Pro Leu Ile His Asp Arg
    1055                1060                1065

Met Leu Met Asp Lys Asn Ala Thr Ala Leu Arg Leu Asn His Met
    1070                1075                1080

Ser Asn Lys Thr Thr Ser Ser Lys Asn Met Glu Met Val Gln Gln
    1085                1090                1095

Lys Lys Glu Gly Pro Ile Pro Pro Asp Ala Gln Asn Pro Asp Met
    1100                1105                1110

Ser Phe Phe Lys Met Leu Phe Leu Pro Glu Ser Ala Arg Trp Ile
    1115                1120                1125

Gln Arg Thr His Gly Lys Asn Ser Leu Asn Ser Gly Gln Gly Pro
    1130                1135                1140

Ser Pro Lys Gln Leu Val Ser Leu Gly Pro Glu Lys Ser Val Glu
    1145                1150                1155

Gly Gln Asn Phe Leu Ser Glu Lys Asn Lys Val Val Val Gly Lys
    1160                1165                1170

Gly Glu Phe Thr Lys Asp Val Gly Leu Lys Glu Met Val Phe Pro
    1175                1180                1185

Ser Ser Arg Asn Leu Phe Leu Thr Asn Leu Asp Asn Leu His Glu
    1190                1195                1200

Asn Asn Thr His Asn Gln Glu Lys Lys Ile Gln Glu Glu Ile Glu
    1205                1210                1215

Lys Lys Glu Thr Leu Ile Gln Glu Asn Val Val Leu Pro Gln Ile
    1220                1225                1230

His Thr Val Thr Gly Thr Lys Asn Phe Met Lys Asn Leu Phe Leu
    1235                1240                1245

Leu Ser Thr Arg Gln Asn Val Glu Gly Ser Tyr Asp Gly Ala Tyr
    1250                1255                1260

Ala Pro Val Leu Gln Asp Phe Arg Ser Leu Asn Asp Ser Thr Asn
    1265                1270                1275

Arg Thr Lys Lys His Thr Ala His Phe Ser Lys Lys Gly Glu Glu
    1280                1285                1290

Glu Asn Leu Glu Gly Leu Gly Asn Gln Thr Lys Gln Ile Val Glu
    1295                1300                1305

Lys Tyr Ala Cys Thr Thr Arg Ile Ser Pro Asn Thr Ser Gln Gln
    1310                1315                1320

Asn Phe Val Thr Gln Arg Ser Lys Arg Ala Leu Lys Gln Phe Arg
    1325                1330                1335

Leu Pro Leu Glu Glu Thr Glu Leu Glu Lys Arg Ile Ile Val Asp
    1340                1345                1350

Asp Thr Ser Thr Gln Trp Ser Lys Asn Met Lys His Leu Thr Pro
    1355                1360                1365

Ser Thr Leu Thr Gln Ile Asp Tyr Asn Glu Lys Glu Lys Gly Ala
    1370                1375                1380

Ile Thr Gln Ser Pro Leu Ser Asp Cys Leu Thr Arg Ser His Ser
    1385                1390                1395

Ile Pro Gln Ala Asn Arg Ser Pro Leu Pro Ile Ala Lys Val Ser
    1400                1405                1410
```

-continued

```
Ser Phe Pro Ser Ile Arg Pro Ile Tyr Leu Thr Arg Val Leu Phe
1415                1420                1425

Gln Asp Asn Ser Ser His Leu Pro Ala Ala Ser Tyr Arg Lys Lys
1430                1435                1440

Asp Ser Gly Val Gln Glu Ser Ser His Phe Leu Gln Gly Ala Lys
1445                1450                1455

Lys Asn Asn Leu Ser Leu Ala Ile Leu Thr Leu Glu Met Thr Gly
1460                1465                1470

Asp Gln Arg Glu Val Gly Ser Leu Gly Thr Ser Ala Thr Asn Ser
1475                1480                1485

Val Thr Tyr Lys Lys Val Glu Asn Thr Val Leu Pro Lys Pro Asp
1490                1495                1500

Leu Pro Lys Thr Ser Gly Lys Val Glu Leu Leu Pro Lys Val His
1505                1510                1515

Ile Tyr Gln Lys Asp Leu Phe Pro Thr Glu Thr Ser Asn Gly Ser
1520                1525                1530

Pro Gly His Leu Asp Leu Val Glu Gly Ser Leu Leu Gln Gly Thr
1535                1540                1545

Glu Gly Ala Ile Lys Trp Asn Glu Ala Asn Arg Pro Gly Lys Val
1550                1555                1560

Pro Phe Leu Arg Val Ala Thr Glu Ser Ser Ala Lys Thr Pro Ser
1565                1570                1575

Lys Leu Leu Asp Pro Leu Ala Trp Asp Asn His Tyr Gly Thr Gln
1580                1585                1590

Ile Pro Lys Glu Glu Trp Lys Ser Gln Glu Lys Ser Pro Glu Lys
1595                1600                1605

Thr Ala Phe Lys Lys Lys Asp Thr Ile Leu Ser Leu Asn Ala Cys
1610                1615                1620

Glu Ser Asn His Ala Ile Ala Ala Ile Asn Glu Gly Gln Asn Lys
1625                1630                1635

Pro Glu Ile Glu Val Thr Trp Ala Lys Gln Gly Arg Thr Glu Arg
1640                1645                1650

Leu Cys Ser Gln Asn Pro Pro Val Leu Lys Arg His Gln Arg Glu
1655                1660                1665

Ile Thr Arg Thr Thr Leu Gln Ser Asp Gln Glu Glu Ile Asp Tyr
1670                1675                1680

Asp Asp Thr Ile Ser Val Glu Met Lys Lys Glu Asp Phe Asp Ile
1685                1690                1695

Tyr Asp Glu Asp Glu Asn Gln Ser Pro Arg Ser Phe Gln Lys Lys
1700                1705                1710

Thr Arg His Tyr Phe Ile Ala Ala Val Glu Arg Leu Trp Asp Tyr
1715                1720                1725

Gly Met Ser Ser Ser Pro His Val Leu Arg Asn Arg Ala Gln Ser
1730                1735                1740

Gly Ser Val Pro Gln Phe Lys Lys Val Val Phe Gln Glu Phe Thr
1745                1750                1755

Asp Gly Ser Phe Thr Gln Pro Leu Tyr Arg Gly Glu Leu Asn Glu
1760                1765                1770

His Leu Gly Leu Leu Gly Pro Tyr Ile Arg Ala Glu Val Glu Asp
1775                1780                1785

Asn Ile Met Val Thr Phe Arg Asn Gln Ala Ser Arg Pro Tyr Ser
1790                1795                1800
```

```
Phe Tyr Ser Ser Leu Ile Ser Tyr Glu Glu Asp Gln Arg Gln Gly
    1805                1810                1815

Ala Glu Pro Arg Lys Asn Phe Val Lys Pro Asn Glu Thr Lys Thr
    1820                1825                1830

Tyr Phe Trp Lys Val Gln His His Met Ala Pro Thr Lys Asp Glu
    1835                1840                1845

Phe Asp Cys Lys Ala Trp Ala Tyr Phe Ser Asp Val Asp Leu Glu
    1850                1855                1860

Lys Asp Val His Ser Gly Leu Ile Gly Pro Leu Leu Val Cys His
    1865                1870                1875

Thr Asn Thr Leu Asn Pro Ala His Gly Arg Gln Val Thr Val Gln
    1880                1885                1890

Glu Phe Ala Leu Phe Phe Thr Ile Phe Asp Glu Thr Lys Ser Trp
    1895                1900                1905

Tyr Phe Thr Glu Asn Met Glu Arg Asn Cys Arg Ala Pro Cys Asn
    1910                1915                1920

Ile Gln Met Glu Asp Pro Thr Phe Lys Glu Asn Tyr Arg Phe His
    1925                1930                1935

Ala Ile Asn Gly Tyr Ile Met Asp Thr Leu Pro Gly Leu Val Met
    1940                1945                1950

Ala Gln Asp Gln Arg Ile Arg Trp Tyr Leu Leu Ser Met Gly Ser
    1955                1960                1965

Asn Glu Asn Ile His Ser Ile His Phe Ser Gly His Val Phe Thr
    1970                1975                1980

Val Arg Lys Lys Glu Glu Tyr Lys Met Ala Leu Tyr Asn Leu Tyr
    1985                1990                1995

Pro Gly Val Phe Glu Thr Val Glu Met Leu Pro Ser Lys Ala Gly
    2000                2005                2010

Ile Trp Arg Val Glu Cys Leu Ile Gly Glu His Leu His Ala Gly
    2015                2020                2025

Met Ser Thr Leu Phe Leu Val Tyr Ser Asn Lys Cys Gln Thr Pro
    2030                2035                2040

Leu Gly Met Ala Ser Gly His Ile Arg Asp Phe Gln Ile Thr Ala
    2045                2050                2055

Ser Gly Gln Tyr Gly Gln Trp Ala Pro Lys Leu Ala Arg Leu His
    2060                2065                2070

Tyr Ser Gly Ser Ile Asn Ala Trp Ser Thr Lys Glu Pro Phe Ser
    2075                2080                2085

Trp Ile Lys Val Asp Leu Leu Ala Pro Met Ile Ile His Gly Ile
    2090                2095                2100

Lys Thr Gln Gly Ala Arg Gln Lys Phe Ser Ser Leu Tyr Ile Ser
    2105                2110                2115

Gln Phe Ile Ile Met Tyr Ser Leu Asp Gly Lys Lys Trp Gln Thr
    2120                2125                2130

Tyr Arg Gly Asn Ser Thr Gly Thr Leu Met Val Phe Phe Gly Asn
    2135                2140                2145

Val Asp Ser Ser Gly Ile Lys His Asn Ile Phe Asn Pro Pro Ile
    2150                2155                2160

Ile Ala Arg Tyr Ile Arg Leu His Pro Thr His Tyr Ser Ile Arg
    2165                2170                2175

Ser Thr Leu Arg Met Glu Leu Met Gly Cys Asp Leu Asn Ser Cys
    2180                2185                2190

Ser Met Pro Leu Gly Met Glu Ser Lys Ala Ile Ser Asp Ala Gln
```

-continued

```
    2195                2200                2205

Ile Thr  Ala Ser Ser Tyr Phe  Thr Asn Met Phe Ala  Thr Trp Ser
    2210                2215                2220

Pro Ser  Lys Ala Arg Leu His  Leu Gln Gly Arg Ser  Asn Ala Trp
    2225                2230                2235

Arg Pro  Gln Val Asn Asn Pro  Lys Glu Trp Leu Gln  Val Asp Phe
    2240                2245                2250

Gln Lys  Thr Met Lys Val Thr  Gly Val Thr Thr Gln  Gly Val Lys
    2255                2260                2265

Ser Leu  Leu Thr Ser Met Tyr  Val Lys Glu Phe Leu  Ile Ser Ser
    2270                2275                2280

Ser Gln  Asp Gly His Gln Trp  Thr Leu Phe Phe Gln  Asn Gly Lys
    2285                2290                2295

Val Lys  Val Phe Gln Gly Asn  Gln Asp Ser Phe Thr  Pro Val Val
    2300                2305                2310

Asn Ser  Leu Asp Pro Pro Leu  Leu Thr Arg Tyr Leu  Arg Ile His
    2315                2320                2325

Pro Gln  Ser Trp Val His Gln  Ile Ala Leu Arg Met  Glu Val Leu
    2330                2335                2340

Gly Cys  Glu Ala Gln Asp Leu  Tyr
    2345                2350

<210> SEQ ID NO 2
<211> LENGTH: 4
<212> TYPE: PRT
<213> ORGANISM: Artificial Sequence
<220> FEATURE:
<223> OTHER INFORMATION: Synthetic

<400> SEQUENCE: 2

Arg His Gln Arg
1
```